United States Patent [19]

Lui

[11] Patent Number: 5,009,895
[45] Date of Patent: Apr. 23, 1991

[54] SUSTAINED RELEASE WITH HIGH AND LOW VISCOSITY HPMC

[75] Inventor: Chung Y. Lui, Lansdale, Pa.

[73] Assignee: Merck & Co., Inc., Rahway, N.J.

[21] Appl. No.: 473,801

[22] Filed: Feb. 2, 1990

[51] Int. Cl.⁵ .................................................. A61K 9/20
[52] U.S. Cl. ..................................... 424/465; 424/494;
424/480
[58] Field of Search ......................... 424/465, 494, 480

[56] References Cited

U.S. PATENT DOCUMENTS

| | | | |
|---|---|---|---|
| 4,806,358 | 2/1989 | Khan | 424/466 |
| 4,837,031 | 6/1989 | Denton | 424/464 |
| 4,871,548 | 10/1989 | Edgren | 424/488 |
| 4,882,164 | 11/1989 | Ferro | 424/450 |

FOREIGN PATENT DOCUMENTS

| | | |
|---|---|---|
| 255404 | 3/1987 | European Pat. Off. . |
| 234670 | 6/1987 | European Pat. Off. . |
| WO87/00044 | 1/1987 | PCT Int'l Appl. . |

*Primary Examiner*—Thurman K. Page
*Assistant Examiner*—D. Gabrielle Phelan
*Attorney, Agent, or Firm*—Melvin Winokur; Joseph F. DiPrima

[57] ABSTRACT

Sustained release formulations are disclosed which contain a therapeutically active medicament and a high and low viscosity HPMC and which exhibit a zero order release profile.

11 Claims, No Drawings

SUSTAINED RELEASE WITH HIGH AND LOW VISCOSITY HPMC

BACKGROUND OF THE INVENTION

Sustained release formulations containing a pharmacologically active agent and exhibiting a zero order release rate are particularly useful.

Ibuprofen is a well-known analgesic which has been used to treat chronic pain such as that associated with arthritic and rheumatic conditions. In such cases the analgesic is best administered so as to sustain its action over a period of time and to have a uniform level of analgesic action over this extended time period. This objective can partly be achieved by the repeated administration of a rapid release dosage. However, this procedure clearly has patient acceptability problems as well as a repeated raising and lowering of the blood levels of analgesic.

Generally, the release profiles in controlled release formulations follow a classical square root of time relationship, i.e., the release rate decreases with time. In a zero order composition a plot of the rate of release of drug vs. time shows a straight horizontal line, i.e., the release rate is independent of time. Zero order sustained release compositions provide a more uniform delivery of the therapeutic agent over long periods of time.

Sustained release formulations for ibuprofen have been disclosed in EP publication No. 255,404, however the formulations disclosed do not provide for a zero order release rate. In WO No. 87/00044 a sustained release formulation, exhibiting a bimodal controlled release, is disclosed. The carrier base is composed of a bimodal hydroxypropylmethylcellulose (HPMC) and the medicament selected from an antiflammatory group such as flurbiprofen. The publication is silent on the formulation of zero order release compositions. The Boots Company PLC, EP No. 234,670 has disclosed a sustained release composition containing xanthan gum wherein the medicament may be ibuprofen. The Boots formulation does not solve the problem of a zero order release rate.

DETAILED DESCRIPTION OF THE INVENTION

The present invention is directed to a carrier base material for therapeutically active medicaments in a solid dosage formulation wherein the carrier base comprises:
   (a) a high viscosity HPMC; and
   (b) a low viscosity HPMC wherein the high and low viscosity HPMC are in a ratio yielding a zero order release profile for the medicament.

In the present invention it has unexpectedly been found that a zero-order release profile can be obtained by controlling the ratio of high to low viscosity HPMC in a carrier base formulation.

A high viscosity HPMC is defined as one having a molecular weight of 60,000 or greater. A low viscosity HPMC is defined as one having a molecular weight of 50,000 or less.

The preferred low viscosity HPMC are available as Dow Methocel cellulose ethers E5, E15LV, E50LV, AND K100LV. The preferred high viscosity HPMC are available as Dow Methocel cellulose ethers E4M CR, E10M CR, K4M, K15M, AND K100M.

The methocel cellulose ethers are characterized by their methoxy and hydroxypropyl content and viscosity as shown in the following table:

| | Methocel Cellulose Ethers | | | | | | | | |
|---|---|---|---|---|---|---|---|---|---|
| | E5 | E15LV | E50LV | K100LV | E4M | E10M | K4M | K15M | K100M |
| Methoxyl % | 28–30 | 28–30 | 28–30 | 19–24 | 19–24 | 28–30 | 19–24 | 19–24 | 19–24 |
| Hydroxypropyl % | 7–12 | 7–12 | 7–12 | 7–12 | 7–12 | 7–12 | 7–12 | 7–12 | 7–12 |
| Viscosity cps (2% in water) | 4–6 | 12–18 | 40–60 | 100 | 4000 | 10,000 | 4000 | 15,000 | 100,000 |

The medicament in the present invention may be selected from ibuprofen, or salts of ibuprofen. Most preferably the medicament is ibuprofen lysine which should be taken to mean all stereoisomeric configurations including racemic ibuprofen lysine and (S)-ibuprofen-(S)-lysine; i.e. the salt formed from (S)-ibuprofen and (S)-lysine.

It should be appreciated that a zero order release profile is obtained only with a certain relative range of high to low viscosity HPMC. This may be illustrated by the combination of 1 part high viscosity E10M CR and a varying amount of any of the preferred low viscosity HPMC wherein a zero order release was found, for example:
(i) 1 part E10M CR: 3 parts E5;
(ii) 1 part E10M CR: 2 to 4 parts E15LV;
(iii) 1 part E10M CR: 3 to 9 parts E50LV;
(iv) 1 part E10M CR: 3 to 9 parts K100LV.

These ranges are not limited to combinations where the high viscosity HPMC is E10M CR but are to be expected with any of the other preferred high viscosity HPMC.

The medicament, preferably ibuprofen lysine is mixed with Povidone USP (PVP) which functions as a binding agent. Typically the ratio of drug to PVP is 20:1.

The percent of drug/PVP granules in the pharmaceutical composition is 33.3 to 83%.

The range of ibuprofen in this invention is preferably 100 to 600 mg per tablet.

Where the medicament is ibuprofen lysine the weight range is 100 to 600 mg measured in mg ibuprofen.

The percent range of HPMC carrier base is 17–66%.

An example of the composition and processing of the controlled release dosage form is provided below:

| Composition: | |
|---|---|
| Ibuprofen Lysine | 61.8% |
| PVP | 3.0% |
| Carrier Base | 34.1% |
| Magnesium Stearate | 1.0% |
| Total | 99.9% |

Fillers such as Avicel, lactose, manitol, dicalcium phosphate, starch or pregelatin starch 1500 may be added to the composition. Binders such as corn starch, pregelatin starch 1500, Klucel LF, methocel E3, E5, gelatin or acacia may be added as necessary by those skilled in the art. Besides magnesium stearate, other lubricants such as stearic acid, sodium stearate fumerate or calcium stearate may be employed.

Processing

A batch of ibuprofen lysine granules containing PVP was prepared. An appropriate amount of granules, typically 3.21 grams was removed and mixed in a V-blender for 10 minutes with a carrier base, usually 1.71 grams, chosen from the preferred high viscosity and low viscosity HPMC. The resultant mixture was then mixed in a V-blender for three minutes with magnesium stearate, which had previously been sieved through a #60 mesh screen. Tablets of about 980 mg were compressed on an F-press.

Tables I-V provide release profiles for controlled release tablets prepared following the processing described above and containing 600 mg Ibuprofen Lysine and 330 mg carrier base. Dissolution determinations were conducted using an automated dissolution testing unit such as a Beckman Spectrophotometer, model DU65, connected with a Vanderkamp 600 six-spindle dissolution tester. Samples were taken every hour for at least 12 to 24 hours and absorbance was read spectrophotometrically at 260 nm.

All the HPMC polymers described are available from the Dow Chemical Company. Racemic ibuprofen lysine may be prepared following the description in U.S. Pat. No. 4,279,926. (S)-ibuprofen-(S)-lysine is prepared as described in copending application Ser. No. 422,466 filed Oct. 18, 1989.

TABLE I

Release Profiles of Ibuprofen Lysine Using 25% E4MCR and 75% of a Low Viscosity HPMC

| Time [hr] | 75% E15LV MEAN ABSORBANCE | 75% E50 MEAN ABSORBANCE | 75% K100LV MEAN ABSORBANCE |
|---|---|---|---|
| 0 | 0.0000 | 0.0000 | 0.0000 |
| 1 | 0.1125 | 0.1160 | 0.0820 |
| 2 | 0.1885 | 0.1935 | 0.1400 |
| 3 | 0.2570 | 0.2615 | 0.1940 |
| 4 | 0.3180 | 0.3230 | 0.2440 |
| 5 | 0.3735 | 0.4080 | 0.2920 |
| 6 | 0.4265 | 0.5290 | 0.3375 |
| 7 | 0.4945 | 0.6265 | 0.3860 |
| 8 | 0.5975 | 0.6820 | 0.4445 |
| 9 | 0.6855 | 0.7190 | 0.5045 |
| 10 | 0.7280 | 0.7405 | 0.5750 |
| 11 | 0.7520 | 0.7555 | 0.6350 |
| 12 | 0.7540 | 0.7620 | 0.6845 |
| 13 | 0.7500 | 0.7675 | 0.7225 |
| 14 | 0.7445 | 0.7680 | 0.7515 |
| 15 | 0.7405 | 0.7670 | 0.7695 |
| 16 | | | 0.7785 |
| 17 | | | 0.7825 |
| 18 | | | 0.7835 |
| 19 | | | |
| 20 | | | |
| 21 | | | |
| 22 | | | |
| 23 | | | |
| 24 | | | |

TABLE II

Release Profiles of Ibuprofen Lysine Using Various Ratios of E10MCR and a Low Viscosity HPMC

| Time [hr] | 25% E10MCR: 75% E5 MEAN ABSORBANCE | 33.3% E10MCR: 66.7% E15LV MEAN ABSORBANCE | 20% E10MCR: 80% E15LV MEAN ABSORBANCE | 25% E10MCR 75% E50 MEAN ABSORBANCE | 10% E10MCR 90% E50LV MEAN ABSORBANCE | 25% E10MCR 75% K100LV MEAN ABSORBANCE | 10% E10MCR 90% K100LV MEAN ABSORBANCE |
|---|---|---|---|---|---|---|---|
| 0 | 0.0000 | 0.0010 | 0.0010 | 0.0000 | 0.0005 | 0.0000 | 0.0005 |
| 1 | 0.0985 | 0.1140 | 0.1615 | 0.1095 | 0.1250 | 0.0790 | 0.1120 |
| 2 | 0.1670 | 0.1720 | 0.2420 | 0.1855 | 0.1960 | 0.1360 | 0.1775 |
| 3 | 0.2335 | 0.2210 | 0.3130 | 0.2570 | 0.2540 | 0.1845 | 0.2325 |
| 4 | 0.3055 | 0.2630 | 0.3760 | 0.3220 | 0.3065 | 0.2300 | 0.2845 |
| 5 | 0.3960 | 0.3050 | 0.4345 | 0.3870 | 0.3580 | 0.2715 | 0.3325 |
| 6 | 0.4800 | 0.3450 | 0.5265 | 0.4505 | 0.4110 | 0.3125 | 0.3825 |
| 7 | 0.5630 | 0.3840 | 0.5975 | 0.5140 | 0.4810 | 0.3525 | 0.4360 |
| 8 | 0.6505 | 0.4220 | 0.6525 | 0.5780 | 0.5475 | 0.3905 | 0.4900 |
| 9 | 0.6875 | 0.4600 | 0.7095 | 0.6220 | 0.5990 | 0.4305 | 0.5595 |
| 10 | 0.7165 | 0.4970 | 0.7475 | 0.6645 | 0.6525 | 0.4730 | 0.6235 |
| 11 | 0.7235 | 0.5345 | 0.7565 | 0.7020 | 0.6885 | 0.5210 | 0.6785 |
| 12 | 0.7255 | 0.5835 | 0.7590 | 0.7255 | 0.7080 | 0.5685 | 0.7170 |
| 13 | 0.7260 | 0.6410 | 0.7600 | 0.7395 | 0.7200 | 0.6045 | 0.7365 |
| 14 | 0.7245 | 0.6915 | 0.7575 | 0.7510 | 0.7275 | 0.6415 | 0.7390 |
| 15 | 0.7240 | 0.7230 | 0.7530 | 0.7560 | 0.7310 | 0.6715 | 0.7370 |
| 16 | 0.7240 | 0.7395 | 0.7525 | 0.7600 | 0.7290 | 0.6905 | 0.7360 |
| 17 | 0.7240 | 0.7425 | 0.7520 | 0.7630 | 0.7260 | 0.7080 | 0.7340 |
| 18 | 0.7245 | 0.7435 | 0.7520 | 0.7650 | 0.7260 | 0.7225 | 0.7360 |
| 19 | 0.7255 | 0.7455 | | 0.7670 | | 0.7345 | |
| 20 | 0.7265 | 0.7440 | | 0.7680 | | 0.7395 | |
| 21 | 0.7275 | 0.7420 | | 0.7700 | | 0.7440 | |
| 22 | 0.7290 | 0.7420 | | 0.7725 | | 0.7450 | |
| 23 | 0.7290 | 0.7410 | | 0.7740 | | | |
| 24 | 0.7310 | 0.7395 | | 0.7755 | | | |

TABLE III

Release Profiles of Ibuprofen Lysine Using Various Ratios of K4M and a Low Viscosity HPMC

| Time [hr] | 50% K4M 50% E5 MEAN ABSORBANCE | 25% K4M 75% E15LV MEAN ABSORBANCE | 25% K4M 75% E5 MEAN ABSORBANCE | 25% K4M 75% K100LV MEAN ABSORBANCE |
|---|---|---|---|---|
| 0 | 0.0000 | 0.0000 | 0.0000 | 0.0000 |
| 1 | 0.1155 | 0.1010 | 0.0995 | 0.0815 |

TABLE III-continued

Release Profiles of Ibuprofen Lysine Using Various Ratios of K4M and a Low Viscosity HPMC

| Time [hr] | 50% K4M 50% E5 MEAN ABSORBANCE | 25% K4M 75% E15LV MEAN ABSORBANCE | 25% K4M 75% E5 MEAN ABSORBANCE | 25% K4M 75% K100LV MEAN ABSORBANCE |
|---|---|---|---|---|
| 2 | 0.1795 | 0.1700 | 0.1565 | 0.1390 |
| 3 | 0.2315 | 0.2335 | 0.2110 | 0.1895 |
| 4 | 0.2815 | 0.2905 | 0.2630 | 0.2365 |
| 5 | 0.3655 | 0.3490 | 0.3130 | 0.2815 |
| 6 | 0.4095 | 0.4360 | 0.4395 | 0.3260 |
| 7 | 0.4465 | 0.5510 | 0.5270 | 0.3705 |
| 8 | 0.4925 | 0.6430 | 0.5815 | 0.4225 |
| 9 | 0.5695 | 0.6990 | 0.6305 | 0.4850 |
| 10 | 0.6550 | 0.7405 | 0.6580 | 0.5435 |
| 11 | 0.7045 | 0.7560 | 0.6775 | 0.6000 |
| 12 | 0.7235 | 0.7565 | 0.6950 | 0.6500 |
| 13 | 0.7360 | 0.7515 | 0.7060 | 0.6740 |
| 14 | 0.7400 | 0.7445 | 0.7175 | 0.6920 |
| 15 | 0.7460 | 0.7415 | 0.7245 | 0.7040 |
| 16 | 0.7535 | 0.7450 | 0.7260 | 0.7220 |
| 17 | 0.7525 | 0.7435 | 0.7275 | 0.7315 |
| 18 | 0.7555 | 0.7415 | 0.7270 | 0.7380 |
| 19 | 0.7605 | 0.7405 | 0.7305 | |
| 20 | 0.7605 | 0.7400 | 0.7305 | |
| 21 | 0.7650 | 0.7425 | 0.7320 | |
| 22 | 0.7635 | | 0.7310 | |
| 23 | 0.7660 | 24 | | |

TABLE IV

Release Profiles of Ibuprofen Lysine Using Various Ratios of K15M and a Low Viscosity HPMC

| Time [hr] | 25% K15M 75% E5 MEAN ABSORBANCE | 25% K15M 75% E15LV MEAN ABSORBANCE | 25% K15M 75% E50 MEAN ABSORBANCE | 25% K15M 75% K100LV MEAN ABSORBANCE |
|---|---|---|---|---|
| 0 | 0.0000 | 0.0000 | 0.0000 | 0.0000 |
| 1 | 0.1280 | 0.0935 | 0.0855 | 0.0950 |
| 2 | 0.2110 | 0.1540 | 0.1425 | 0.1640 |
| 3 | 0.2830 | 0.2085 | 0.1915 | 0.2225 |
| 4 | 0.3640 | 0.2590 | 0.2390 | 0.2740 |
| 5 | 0.4350 | 0.3070 | 0.2810 | 0.3215 |
| 6 | 0.5060 | 0.3530 | 0.3265 | 0.3665 |
| 7 | 0.6475 | 0.3980 | 0.3970 | 0.4120 |
| 8 | 0.7215 | 0.4470 | 0.4890 | 0.4575 |
| 9 | 0.7360 | 0.5505 | 0.5535 | 0.5040 |
| 10 | 0.7415 | 0.6200 | 0.5945 | 0.5485 |
| 11 | 0.7410 | 0.6655 | 0.6125 | 0.5910 |
| 12 | 0.7395 | 0.6815 | 0.6400 | 0.6245 |
| 13 | 0.7435 | 0.6850 | 0.6590 | 0.6490 |
| 14 | 0.7475 | 0.7040 | 0.6910 | 0.6650 |
| 15 | 0.7490 | 0.7250 | 0.7085 | 0.6845 |
| 16 | 0.7520 | 0.7365 | 0.7295 | 0.7035 |
| 17 | 0.7505 | 0.7395 | 0.7395 | 0.7160 |
| 18 | 0.7515 | 0.7390 | 0.7400 | 0.7235 |
| 19 | 0.7485 | 0.7405 | 0.7330 | 0.7305 |
| 20 | 0.7525 | 0.7405 | 0.7355 | 0.7345 |
| 21 | 0.7500 | 0.7360 | 0.7255 | 0.7385 |
| 22 | | | | 0.7415 |

TABLE V

Release Profiles of Ibuprofen Lysine Using 25% K100M and 75% of a Low Viscosity HPMC.

| Time [hr] | 75% E15LV MEAN ABSORBANCE | 75% E50 MEAN ABSORBANCE |
|---|---|---|
| 0 | 0.0000 | 0.0000 |
| 1 | 0.0820 | 0.1005 |
| 2 | 0.1330 | 0.1615 |
| 3 | 0.1800 | 0.2180 |
| 4 | 0.2225 | 0.2680 |
| 5 | 0.2630 | 0.3150 |
| 6 | 0.3025 | 0.3630 |
| 7 | 0.3405 | 0.4230 |
| 8 | 0.3805 | 0.4950 |
| 9 | 0.4240 | 0.5465 |
| 10 | 0.4880 | 0.5940 |
| 11 | 0.5510 | 0.6350 |
| 12 | 0.5945 | 0.6715 |
| 13 | 0.6335 | 0.7000 |
| 14 | 0.6650 | 0.7215 |
| 15 | 0.6950 | 0.7370 |
| 16 | 0.7195 | 0.7485 |
| 17 | 0.7395 | 0.7575 |
| 18 | 0.7530 | 0.7655 |
| 19 | 0.7680 | 0.7710 |

TABLE V-continued

Release Profiles of Ibuprofen Lysine Using 25% K100M and 75% of a Low Viscosity HPMC.

| Time [hr] | 75% E15LV MEAN ABSORBANCE | 75% E50 MEAN ABSORBANCE |
|---|---|---|
| 20 | 0.7740 | 0.7755 |
| 21 | 0.7795 | 0.7770 |
| 22 | 0.7825 | 0.7785 |
| 23 |  | 0.7800 |
| 24 |  | 0.7820 |

What is claimed is:

1. A carrier base material combined with a therapeutically active medicament and shaped and compressed to a solid sustained release pharmaceutical dosage form having a zero order release profile upon administration, carrier base material comprising:
   (a) a high viscosity HPMC; having a molecular weight of 60,000 or greater; and
   (b) a low viscosity HPMC, having a molecular weight of 50,000 or less, wherein the high and low viscosity HPMC are in a ratio yielding a zero order release profile.

2. A zero order release pharmaceutical formulation according to claim 1 in which the high viscosity HPMC is selected from a methocel cellulose ether wherein:
   (a) % methoxy=19-24, % hydroxypropyl=7-12, viscosity=4000 cps;
   (b) % methoxy=28-30, % hydroxypropyl=7-12, viscosity=10,000;
   (c) % methoxy=19-24, % hydroxypropyl=7-12, viscosity=4,000;
   (d) % methoxy=19-24, % hydroxypropyl=7-12, viscosity=15,000;
   (e) % methoxy=19-24, % hydroxypropyl=7-12, viscosity=100,000;
   and the low viscosity HPMC is selected from a methocel cellulose ether wherein:
   (a) % methoxy=28-30, % hydroxypropyl=7-12, viscosity=4-6;
   (b) % methoxy=28-30, % hydroxypropyl=7-12, viscosity=12-18;
   (c) % methoxy=28-30, % hydroxypropyl=7-12, viscosity=40-60;
   (d) % methoxy=19-24, % hydroxypropyl=7-12, viscosity=100.

3. A zero order release pharmaceutical formulation according to claim 2 wherein the high viscosity HPMC is 1 part methocel cellulose ether wherein % methoxy=28-30, % hydroxypropyl=7-12 and viscosity=10,000 and wherein the low viscosity HPMC is selected from;
   (a) 3 parts wherein % methoxy=28-30, % hydroxypropyl=7-12, and viscosity=4-6;
   (b) 2 to 4 parts wherein % methoxy=28-30, % hydroxypropyl=7-12, and viscosity=12-18;
   (c) 3 to 9 parts wherein % methoxy=28-30, % hydroxypropyl=7-12, and viscosity=40-60; or
   (d) 3 to 9 parts wherein % methoxy=19-24, % hydroxypropyl=7-12, and viscosity=100.

4. A zero order release pharmaceutical formulation according to claim 2 wherein the high viscosity HPMC is 1 part wherein % methoxy=19-24, % hydroxypropyl=7-12, and viscosity=4,000 and wherein the low viscosity HPMC is selected from:
   (a) 2 to 4 parts wherein % methoxy=28-30, % hydroxypropyl=7-12, and viscosity=12-18;
   (b) 3 to 9 parts wherein % methoxy=28-30, % hydroxypropyl=7-12, and viscosity=40-60;
   (c) 3 to 9 parts wherein % methoxy=19-24, % hydroxypropyl=7-12, and viscosity=100.

5. A zero order release pharmaceutical formulation according to claim 2 wherein the high viscosity HPMC is 1 part wherein % methoxy=19-24, % hydroxypropyl=7-12, and viscosity=4,000 and wherein the low viscosity HPMC is selected from:
   (a) 1 part wherein % methoxy=28-30, % hydroxypropyl=7-12, and viscosity=4-6;
   (b) 2 to 4 parts wherein % methoxy=28-30, % hydroxypropyl=7-12, and viscosity=12-18;
   (c) 3 to 9 parts wherein % methoxy=28-30, % hydroxypropyl=7-12, and viscosity=40-60;
   (d) 3 to 9 parts wherein % methoxy=19-24, % hydroxypropyl=7-12, and viscosity=100.

6. A zero order release pharmaceutical formulation according to claim 2 wherein the high viscosity HPMC is one part wherein % methoxy=19-24, % hydroxypropyl=7-12, and viscosity=15,000 and wherein the low viscosity HPMC is selected from:
   (a) 1 to 3 parts wherein % methoxy=28-30, % hydroxypropyl=7-12, and viscosity=4-6;
   (b) 1 to 3 parts wherein % methoxy=28-30, % hydroxypropyl=7-12, and viscosity=12-18;
   (c) 1 to 3 parts wherein % methoxy=28-30, % hydroxypropyl=7-12, and viscosity=40-60;
   (d) 3 to 9 parts wherein % methoxy=19-24, % hydroxypropyl=7-12, and viscosity=100.

7. A zero order release pharmaceutical formulation according to claim 2 wherein the high viscosity HPMC is 1 part wherein % methoxy=19-24, % hydroxypropyl=7-12 and viscosity=100,000 and wherein the low viscosity HPMC is selected from:
   (a) 1 to 3 parts wherein % methoxy=28-30, % hydroxypropyl=7-12, and viscosity=12-18;
   (b) 1 to 3 parts wherein % methoxy=28-30, % hydroxypropyl=7-12, and viscosity=40-60.

8. A zero order release pharmaceutical formulation according to claim 2 wherein the medicament is selected from:
   (a) ibuprofen; or
   (b) salts of ibuprofen 9. A formulation according to claim 8 wherein the medicament is ibuprofen lysine.

10. A formulation according to claim 9 wherein the medicament is (S)-ibuprofen-(S)-lysine.

11. A formulation according to claim 10 wherein the amount of medicament as ibuprofen is 100 to 600 mg.

* * * * *